United States Patent
Moller et al.

(10) Patent No.: US 11,634,775 B2
(45) Date of Patent: Apr. 25, 2023

(54) CIRCULATING SERUM MICRORNA BIOMARKERS AND METHODS FOR ALZHEIMER'S DISEASE DIAGNOSIS

(71) Applicant: ST. JOHN'S UNIVERSITY, Queens, NY (US)

(72) Inventors: Simon Geir Moller, Queens, NY (US); Ketan Shirish Patil, Queens, NY (US); Guido Werner Alves, Queens, NY (US)

(73) Assignee: ST. JOHN'S UNIVERSITY, Queens, NY (US)

( * ) Notice: Subject to any disclaimer, the term of this patent is extended or adjusted under 35 U.S.C. 154(b) by 17 days.

(21) Appl. No.: 16/623,937

(22) PCT Filed: Jun. 7, 2018

(86) PCT No.: PCT/US2018/036377
§ 371 (c)(1),
(2) Date: Dec. 18, 2019

(87) PCT Pub. No.: WO2018/236589
PCT Pub. Date: Dec. 27, 2018

(65) Prior Publication Data
US 2020/0190588 A1 Jun. 18, 2020

Related U.S. Application Data

(60) Provisional application No. 62/521,768, filed on Jun. 19, 2017.

(51) Int. Cl.
*C12Q 1/6883* (2018.01)

(52) U.S. Cl.
CPC ..... *C12Q 1/6883* (2013.01); *C12Q 2600/158* (2013.01); *C12Q 2600/178* (2013.01); *G01N 2800/2821* (2013.01)

(58) Field of Classification Search
None
See application file for complete search history.

(56) References Cited

U.S. PATENT DOCUMENTS

| | | |
|---|---|---|
| 2012/0108650 A1 | 5/2012 | Jin et al. |
| 2013/0040303 A1 | 2/2013 | Wang |
| 2014/0206777 A1 | 7/2014 | Goren |
| 2014/0378439 A1 | 12/2014 | Dezso |
| 2016/0273043 A1 | 9/2016 | Umanksy |
| 2018/0067132 A1 | 3/2018 | Tahara |

FOREIGN PATENT DOCUMENTS

| | | |
|---|---|---|
| JP | 2014-520529 A | 8/2014 |
| JP | 2016-538851 A | 12/2016 |
| WO | 2009/009457 | 1/2009 |
| WO | 2013/003350 | 1/2013 |
| WO | 2013/022953 | 2/2013 |
| WO | 2013/024469 | 2/2013 |
| WO | 2015/179909 A1 | 12/2015 |
| WO | 2016/148073 A1 | 9/2016 |

OTHER PUBLICATIONS

Thisted (The University of Chicago 1998).*
Liang (BMC Genomics 2007 8:166 pp. 1-20).*
Patil (Parkinsonism and Related Disorders 64 2019 202-210 e-pub Apr. 11, 2019).*
Skurnikov (Bulletin of Experimental Biology and Medicine vol. 160 No. 5 Mar. 2016 General Pathology and Pathophysiology).*
Lugli (PLOS ONE 10(10) e0139233 pp. 1-18 Oct. 2015).*
Wang (PloS ONE Jul. 2012 7(7);e41561).*
Wolenski (Journal of Applied Toxicology 2017; 37:278-286).*
Geekiyanage et al., "Blood serum miRNA: Non-invasive biomarkers for Alzheimer's disease", Experimental Neurology, vol. 235, No. 2 (2012) 491-6.
Li, Fei et al., MicroRNA-574 is involved in cognitive impairment in 5-month-old APP/PS1 mice through regulation of neuritin, Brain Research 2015, vol. 1627, pp. 177-188.

* cited by examiner

*Primary Examiner* — Amanda Haney
(74) *Attorney, Agent, or Firm* — Venable LLP

(57) ABSTRACT

Biomarkers and methods for identifying, verifying and confirming circulating serum-based microRNAs. The microRNAs (PARKmiRs) can be used to differentiate patient's suffering from Alzheimer's disease (AD) from non-AD patients.

17 Claims, 2 Drawing Sheets

Specification includes a Sequence Listing.

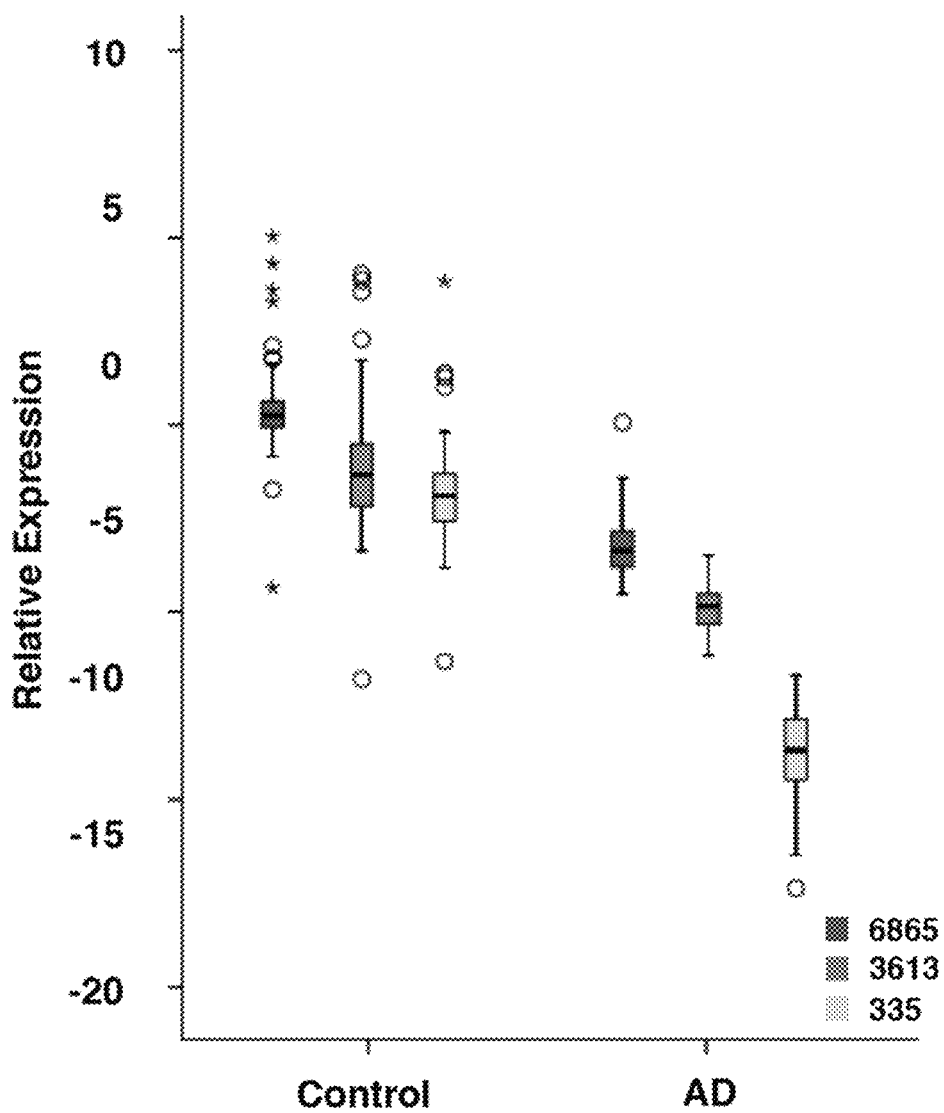
Figure 1: Specificity of PARKmiRs. Plot for qRT-PCR data showing distinct expression (log) patterns observed for PARKmiRs in 50 AD patient serum samples as compared to 182 control serum samples.

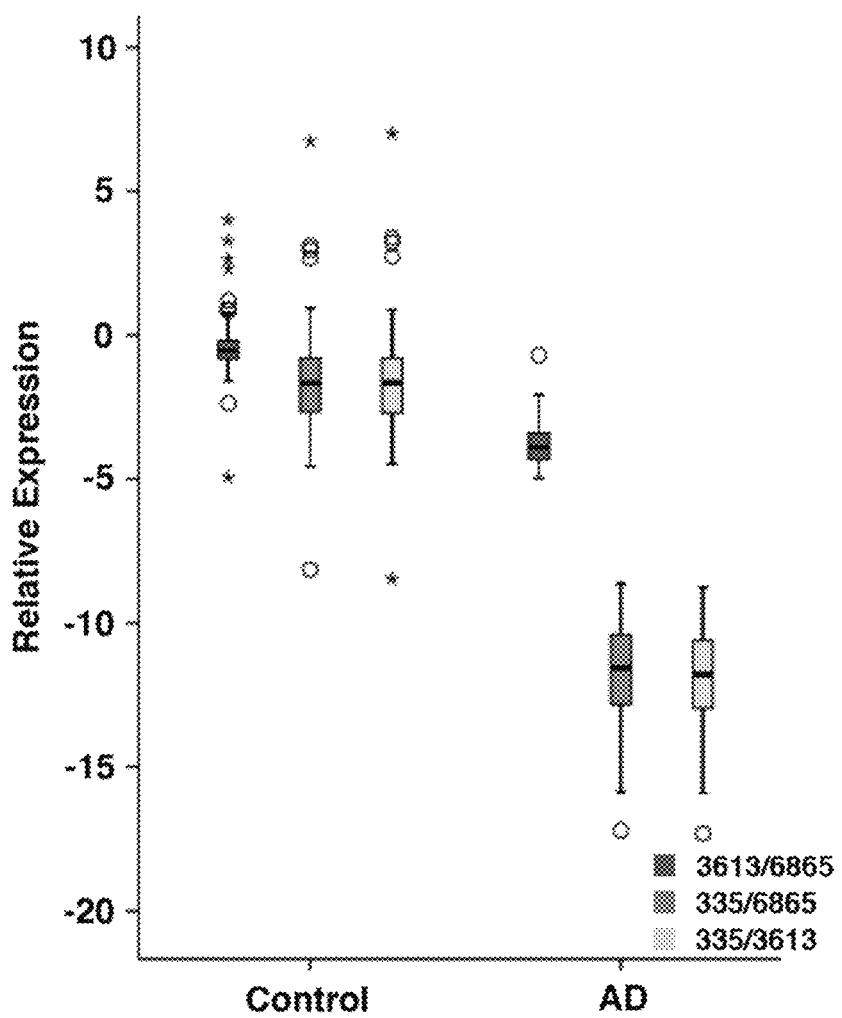
Figure 2: Specificity of PARKmiR combinations. Plot for qRT-PCR data showing distinct expression (log) patterns observed for PARKmiR combinations in 50 AD patient serum samples as compared to 182 control serum samples.

CIRCULATING SERUM MICRORNA BIOMARKERS AND METHODS FOR ALZHEIMER'S DISEASE DIAGNOSIS

This application is a national phase of PCT Application No. PCT/US2018/036377 filed Jun. 7, 2018, which in turn claims benefit of U.S. Provisional Patent Application No. 62/521,768 filed Jun. 19, 2017, which are hereby incorporated by reference herein in their entirety.

BACKGROUND OF THE INVENTION

1. Field of the Invention

The present invention generally relates to serum-based microRNAs and methods for differentiating patients suffering from Alzheimer's disease, as well as assisting clinicians to determine treatment protocols for such patients.

2. Brief Description of the Background Art

Alzheimer's disease (AD), the most common neurodegenerative disease, is characterized by loss of memory and other cognitive abilities of an individual with treatment available for only symptomatic relief. Alzheimer's is a progressive disease, which advances with increasingly severe symptoms including mood and behavior changes; difficulty speaking, swallowing and walking; disorientation and more serious memory loss. The drug combinations in use are only palliative but cannot reverse the process of neuronal cell death. There are neither any objective tests nor any established biomarkers for the diagnosis of AD. Further, the heterogeneity, subtypes and the progression of the disease makes it even complex to develop specific therapeutic candidates. Thus it is imperative to diagnose disease at the early stage to increase the efficacy of therapeutic agents.

AD and AD related dementia currently affects about 44 million people world-wide. Effective management of a patient with AD is possible in the initial years of treatment, after which time a series of often debilitating complications occur. Current treatment for AD includes multi-drug regiment including cholinesterase inhibitors, Antidepressants, Anxiolytics, Antipsychotic medications, and sedatives to treat a specific symptom. There are many new drugs being developed that can alter the disease process itself by targeting AD-related proteins and processes including beta-amyloid, beta-secretase, Tau-protein, inflammation, and the 5HT6 receptor amongst others.

In the brain, neurons connect and communicate at synapses, where tiny bursts of chemicals called neurotransmitters carry information from one cell to another. Neurons are the chief cells destroyed by Alzheimer's disease. Accordingly, Alzheimer's disease destroys synapses and kills neurons, damaging and eventually destroying the brain's communication network.

Current FDA-approved Alzheimer's drugs support this communication process through two different mechanisms:
1) Cholinesterase inhibitors work by slowing down the process that breaks down a key neurotransmitter. Specifically, cholinesterase inhibitors boost levels of cell-to-cell communication by providing the neurotransmitter acetylcholine that is depleted in the brain by Alzheimer's disease. Donepezil, galantamine and rivastigmine are cholinesterase inhibitors.
2) Memantine is an NMDA (N-methyl-D-aspartate) receptor antagonist and works by regulating the activity of glutamate, a neurotransmitter in the brain. Attachment of glutamate to cell surface NMDA receptors permits calcium to enter the cell. This process is important for cell signaling, as well as learning and memory. In Alzheimer's disease, excess glutamate can be released from damaged cells, leading to chronic overexposure to calcium, which can speed up cell damage. Memantine helps prevent this destructive chain of events by partially blocking the NMDA receptors.

Although the effectiveness of cholinesterase inhibitors and memantine varies widely across the population, it is imperative to diagnose individuals with AD at an early stage to increase the efficacy of therapeutic agents. However, there are neither any objective tests nor established biomarkers for diagnosing AD. Moreover, the heterogeneity, subtypes and progression of the disease make it difficult to develop specific therapeutic candidates.

MicroRNAs ("miRNAs") are a class of non-coding RNAs that play key roles in the regulation of gene expression. miRNAs act at the post-transcriptional level and fine-tune the expression of as much as 30% of all mammalian protein-encoding genes. Mature miRNAs are short, single-stranded RNA molecules approximately 22 nucleotides in length. miRNAs may be encoded by multiple loci, and may be organized in tandemly co-transcribed clusters. miRNA genes are transcribed by RNA polymerase II as large primary transcripts (pri-microRNA) that are processed by a protein complex containing the RNase III enzyme Drosha, DGCR8 and other cofactors, to form an approximately 70 nucleotide precursor microRNA (pre-miRNA). (Cathew R W, Cell, 2009; Kim V N, Nat Rev Mol Cel Biol, 2009; Siomi H, Mol Cel, 2010; Bartel D P, Cell, 2004; Lee Y, Nature 2003; Han J, Genes Dev, 2004.) Pre-miRNA is transported to the cytoplasm by Exportin-5 where it is processed by DICER, a second RNase III enzyme, together with TRBP, PACT and Ago2 in the RNA Induced Silencing Complex resulting in miRNA duplexes (Kim V N, Nat Rev Mol Cel Biol, 2009; Gregory R I, Nature 2004; MAcRae I J, PNAS, 2008). The guide strands of miRNA duplexes separate and associate with Ago 2 for incorporation into a ribonuclear particle to form the RNA-induced silencing complex RISC that mediates gene silencing. The mechanisms of miRNA range from direct degradation or silencing of mRNA and repression of translation to post-transcriptional upregulations. (MacRae I J, PNAS, 2008.)

The presence of miRNAs has been reported in body fluids including blood, cerebrospinal fluid (CSF), plasma, serum and saliva at detectable levels. The tissue-specificity of miRNAs suggests their vital and integral role in various physiological processes. The tissue-enrichment promises a new but less explored role as diagnostic biomarker and potential therapeutic target. Circulating miRNAs are understood to originate from passive leakage from damaged tissue as a result of cell lysis or apoptosis, active transport from cells via microvesicles, such as exosomes, or bound within RISC protein complexes (Etheridge et al, 2011). Exosome and osmotic pump-mediated delivery of small RNA molecules to the brain and CNS, respectively, provides a solution to overcoming the limitations of miRNA-based therapies (Alvarez-Erviti et al., 2011; Koval et al, 2013, Hum. Mol. Gen). miRNA has been demonstrated to be exceptionally stable and thus present as powerful candidates to be potential biomarkers (Chen et al, 2008; Grasso, 2014).

SUMMARY OF THE INVENTION

It is an object of the present invention to identify miRNAs relevant to patients suffering from Alzheimer's disease.

It is another object of the present invention to provide methods for determining patients suffering from Alzheimer's disease.

These objects and others are achieved by the present invention, which provides miRNA biomarkers that may be used singly, in pairs or in combination to determine patients suffering from Alzheimer's disease.

BRIEF DESCRIPTION OF THE DRAWINGS

FIG. 1 shows the mean fold change of three PARKmiR-NAs between AD patients and healthy controls;

FIG. 2 shows the mean fold change of three combinations of PARKmiRNAs between AD patients and healthy controls;

DETAILED DESCRIPTION OF THE INVENTION

We performed microarray analysis (discovery phase from the Norwegian ParkWest study), confirmation by qRT-PCR (same samples from discovery phase), verification by qRT-PCR (large sample set from the Norwegian Parkwest study) and validation by qRT-PCR (independent cohort from the Swedish NYPUM study) on control and PD serum samples at baseline as described in the PD diagnostic patent. All this data was generated and discussed in U.S. Application No. 62/291,619 filed Feb. 5, 2016 and International Application No. PCT/US2017/016412 filed Feb. 3, 2017, the disclosures of which are hereby incorporated herein by reference.

During data collection for the diagnostic PD miRNA project we also tested the candidate miRNAs (PARKmiRs) for specificity using 45 serum samples from newly diagnosed AD patients from the DemVest study representing the same region in Norway as for the PD population in the Parkwest study. The inventors expected that the PARKmiRs would show the same abundance levels as in control serum samples, which would verify specificity of the PARKmiRs to PD. Unexpectedly the PARKmiRs showed a significant decrease in levels in the AD serum samples as compared to control serum samples. To ensure that the AD serum samples and the techniques used were valid we tested whether miR-445-3p and control small RNA (U6) changed in abundance. In control serum, PD serum and AD serum both miRNAs remained unchanged in abundance validating our findings.

Methods

Serum Samples Handling and Classification

All patients and controls participated in the Norwegian ParkWest study and the Dementia Study of Western Norway (DemVest study) which are ongoing prospective population-based longitudinal cohort studies investigating the incidence, neurobiology and prognosis of PD and dementia/AD, respectively. The Norwegian ParkWest study is a prospective longitudinal multicenter cohort study of patients with incident Parkinson's disease (PD) from Western and Southern Norway, Between Nov. 1, 2004 and 31 Aug. 2006 it was endeavored to recruit all new cases of Parkinson Disease within the study area. Since the start of the study 212 of 265 (80%) of these patients and their age-/sex-matched control group have been followed. Further information about this project can be found at http://www.parkvest.no. The Dementia Study of Western Norway is a prospective longitudinal multicenter cohort study of patients with a first-time dementia diagnosis (Mini Mental State Examination (MMSE) score>15). Patient recruitment started in 2005 and patients were followed annually. Patients with acute delirium or confusion, terminal illness, or current or previous bipolar disorder or psychotic disorder, or who were recently diagnosed with a major somatic illness, were excluded from the study.

All possible efforts were undertaken to establish an unselected and population-representative cohort of patients with AD. Patients were included if they had provided serum at study entry and fulfilled diagnostic criteria for AD according to the National Institute of Neurological and Communicative Diseases and Stroke/Alzheimer's Disease and Related Disorders Association (NINCDS/ARDRA) criteria at latest follow-up. Control subjects were recruited from multiple sources, including friends, spouses, and public organizations for elderly and were included in this study if they had provided serum. In this study of possible biomarkers for AD we applied a two-stage procedure. For the first discovery phase serum from 16 patients and 8 controls were selected at random. The remaining 45 patients with AD and 182 controls that were eligible for this study were selected for verification purposes. Serum samples were collected at the same day as the clinical examinations and then stored frozen at −70 degrees Celsius until transported to the facilities in New York on dry ice.

Example 1

Analyses of Differentially Expressed Human miRNA by qPCR

RNA Isolation from Serum Samples and QC

After thawing on ice, twenty-four (eight control, sixteen PD samples) serum samples were spun down for 5 mins at 3000×g to remove debris. The supernatant was used to perform small RNA isolation using miRCURY RNA Isolation Kit—Biofluids (Exiqon, MA). Before RNA Isolation, the lysis buffer was spiked with 0.267 fmol/ul of spike-in control cel-miR-39-3p (Qiagen, Calif.).

The remaining part of the RNA isolation was performed following the manufacturer's protocol and the isolated RNA was quantified on a Nanodrop 2000 (Thermo Scientific, MA). The RNA was used for running Affymetrix v4 microRNA microarray chips and for subsequent cDNA synthesis and qPCR. RNA from 256 serum samples (190 control, 16 PD from ParkWest project 45 AD from the DemVest project) was isolated as described above, they were not quantified by Nanodrop, but the qPCR data resulting from these samples were normalized by a reference small RNA scaRNA17.

miRNA Microarray and Data Analysis

The isolated RNA from twenty-four patient serum samples were quantified and subjected to Affymetrix GeneChip® miRNA 4.0 Array by the Yale Center for Genome Analysis (http://medicine.yale.edu/keck/ycga/index.aspx). The normalized .CEL files obtained from Affymetrix Expression Console software were imported into Partek Genomics Suite version 6.6 Copyright © 2012 (Partek, MO) for analysis. The 'microRNA Expression Workflow' was employed to detect differentially expressed miRNAs employing ANOVA resulting in lists of miRNAs significantly (p<0.05) expressed between control versus PD cohorts. The miRNAs detected were used for further qPCR verification.

Quantitative Polymerase Chain Reaction cDNA for miRNA specific qPCR was synthesized using qScript™ microRNA cDNA Synthesis kit (Quanta Biosciences, MD) following manufacturer's protocol and subsequent qPCRs were performed using miRNA specific forward primers (Table #) and PerfeCTa® Universal PCR primer (Quanta Biosciences, MD). scaRNA17 and U6 were used reference small RNAs for normalizing qPCR Cq values whereas cel-miR-39-3p was used as spike-in control. PerfeCTa® SYBR® GREEN SuperMix for IQ™ (Quanta Biosciences, MD) was used for all qPCRs in a MyiQ™ Single color Real-Time PCR Detection System (Bio-Rad, CA). Standard curve for cel-miR-39-3p was analyzed in MS Excel with $R^2=0.97882$ and PCR efficiency 92.96%. No Template Control (NTC) was implied wherever needed.

Data Analysis Based on PD Model

The discriminative ability of miRNAs with regard to PD diagnosis was assessed from ROC analysis using IBM SPSS Statistics, version 21; for combinations of miRNAs the test variable was the predicted probability from logistic regression with PD diagnosis (yes/no) as outcome. To minimize the influence of outlying values on the fit, logistic regression was performed with log transformed miRNA values.

Differentially expressed human miRNAs in PD patients' serum samples from The Norwegian ParkWest study were determined employing miRNA microarray. Provided below are the miRNAs with >1.2 fold differential expression.

85 Differentially Expressed Human Pre- and Mature miRNAs with >1.2 Fold Change hsa-miR-548ac, hsa-miR-335-5p, hsa-miR-548x-3p, hsa-miR-520g, hsa-miR-520h, hsa-miR-548ae, hsa-miR-3910-1, hsa-miR-4708-3p, hsa-miR-16-2-3p, hsa-miR-603, hsa-miR-3613-3p, hsa-miR-4797-5p, hsa-miR-548aj-3p, hsa-miR-450b-5p, hsa-miR-548ap-3p, hsa-miR-1184, hsa-miR-2277-5p, hsa-miR-1323, hsa-miR-548aa, hsa-miR-548t-3p, hsa-miR-221-5p, hsa-miR-190a-3p, hsa-miR-6873-5p, hsa-miR-155-3p, hsa-miR-510-5p, hsa-miR-4313, hsa-miR-3616, hsa-miR-8075, hsa-miR-4306, hsa-miR-6776, hsa-miR-6075, hsa-miR-8052, hsa-miR-532, hsa-miR-4791, hsa-miR-320b-1, hsa-miR-548y, hsa-miR-7973, hsa-miR-3136-5p, hsa-miR-606, hsa-miR-500a-3p, hsa-miR-4788, hsa-miR-4769-3p, hsa-miR-299-5p, hsa-miR-4431, hsa-miR-6749-5p, hsa-miR-138-2-3p, hsa-miR-1289-2, hsa-miR-548au, hsa-miR-6850, hsa-miR-561, hsa-miR-34b-5p, hsa-miR-3934-5p, hsa-miR-6739-5p, hsa-miR-4325, hsa-miR-4672, hsa-miR-215-5p, hsa-miR-4685-5p, hsa-miR-3160-1, hsa-miR-3160-2, hsa-miR-6793-5p, hsa-miR-8089, hsa-miR-6081, hsa-miR-892b, hsa-miR-936, hsa-miR-548ag, hsa-miR-345, hsa-miR-548k, hsa-miR-3188, hsa-miR-181b-5p, hsa-let-7e, hsa-miR-4487, hsa-miR-509-3p, hsa-miR-3689a-3p, hsa-miR-4771, hsa-miR-520a-5p, hsa-miR-3150b, hsa-miR-6782-5p, hsa-miR-93'7-5p, hsa-miR-455-3p, hsa-miR-6865-3p, hsa-miR-4749-5p, hsa-miR-378b, hsa-miR-7706, hsa-miR-4445 and hsa-miR-2355-5p.

57 Differentially Expressed Mature miRNAs with >1.2 Fold Change hsa-miR-548ac, hsa-miR-335-5p, hsa-miR-548x-3p, hsa-miR-548ae, hsa-miR-4'708-3p, hsa-miR-16-2-3p, hsa-miR-603, hsa-miR-3613-3p, hsa-miR-4797-5p, hsa-miR-548aj-3p, hsa-miR-450b-5p, hsa-miR-548ap-3p, hsa-miR-1184, hsa-miR-2277-5p, hsa-miR-1323, hsa-miR-548aa, hsa-miR-548t-3p, hsa-miR-221-5p, hsa-miR-190a-3p, hsa-miR-6873-5p, hsa-miR-155-3p, hsa-miR-510-5p, hsa-miR-4313, hsa-miR-4306, hsa-miR-8052, hsa-miR-4791, hsa-miR-7973, hsa-miR-3136-5p, hsa-miR-606, hsa-miR-500a-3p, hsa-miR-4769-3p, hsa-miR-299-5p, hsa-miR-6749-5p, hsa-miR-138-2-3p, hsa-miR-34b-5p, hsa-miR-3934-5p, hsa-miR-6739-5p, hsa-miR-4325, hsa-miR-215-5p, hsa-miR-4685-5p, hsa-miR-6793-5p, hsa-miR-936, hsa-miR-548ag, hsa-miR-548k, hsa-miR-181b-5p, hsa-let-7e, hsa-miR-509-3p, hsa-miR-3689a-3p, hsa-miR-4771, hsa-miR-520a-5p, hsa-miR-6782-5p, hsa-miR-93'7-5p, hsa-miR-455-3p, hsa-miR-6865-3p, hsa-miR-4749-5p, hsa-miR-378b and hsa-miR-2355-5p.

28 Differentially Expressed Premature miRNAs with >1.2 Fold Change hsa-miR-520g, hsa-miR-520h, hsa-miR-3910-1, hsa-miR-3616, hsa-miR-8075, hsa-miR-6776, hsa-miR-6075, hsa-miR-532, hsa-miR-320b-1, hsa-miR-548y, hsa-miR-4788, hsa-miR-4431, hsa-miR-1289-2, hsa-miR-548au, hsa-miR-6850, hsa-miR-561, hsa-miR-4672, hsa-miR-3160-1, hsa-miR-3160-2, hsa-miR-8089, hsa-miR-6081, hsa-miR-892b, hsa-miR-345, hsa-miR-3188, hsa-miR-4487, hsa-miR-3150b, hsa-miR-7706 and hsa-miR-4445.

These differentially expressed miRNA sequences are illustrated below in Table 1, along with the reference/housekeeping small RNAs cel-miR-39-3p, U6 and ScaRNA17 used as controls. Cel-miR-39-3p is a spike-in control that demonstrates the stability of the RNA samples. U6 and ScaRNA17 are used as internal controls to normalize the readings of the rest of the miRNAs or candidate miRNAs.

TABLE 1

| microRNA/small RNA name | microRNA Sequence |
|---|---|
| cel-miR-39-3p | UCACCGGGUGUAAAUCAGCUUG (SEQ ID NO: 1) |
| hsa-let-7e | CCCGGGCUGAGGUAGGAGGUUGUAUAGUUGAGGAGGACACCC AAGGAGAUCACUAUACGGCCUCCUAGCUUUCCCCAGG (SEQ ID NO: 2) |
| hsa-miR-1184 | CCUGCAGCGACUUGAUGGCUUCC (SEQ ID NO: 3) |
| hsa-miR-1289-2 | CCACGGUCCUAGUUAAAAAGGCACAUUCCUAGACCCUGCCUC AGAACUACUGAACAGAGUCACUGGGUGUGGAGUCCAGGAAUC UGCAUUUUUACCCCUAUCGCCCCCGCC (SEQ ID NO: 4) |
| hsa-miR-1323 | UCAAAACUGAGGGGCAUUUUCU (SEQ ID NO: 5) |
| hsa-miR-138-2-3p | GCUAUUUCACGACACCAGGGUU (SEQ ID NO: 6) |
| hsa-miR-155-3p | CUCCUACAUAUUAGCAUUAACA (SEQ ID NO: 7) |
| hsa-miR-16-2-3p | CCAAUAUUACUGUGCUGCUUUA (SEQ ID NO: 8) |
| hsa-miR-181b-5p | AACAUUCAUUGCUGUCGGUGGGU (SEQ ID NO: 9) |

TABLE 1-continued

| microRNA/small RNA name | microRNA Sequence |
|---|---|
| hsa-miR-190a-3p | CUAUAUAUCAAACAUAUUCCU (SEQ ID NO: 10) |
| hsa-miR-215-5p | AUGACCUAUGAAUUGACAGAC (SEQ ID NO: 11) |
| hsa-miR-221-5p | ACCUGGCAUACAAUGUAGAUUU (SEQ ID NO: 12) |
| hsa-miR-2277-5p | AGCGCGGGCUGAGCGCUGCCAGUC (SEQ ID NO: 13) |
| hsa-miR-2355-5p | AUCCCCAGAUACAAUGGACAA (SEQ ID NO: 14) |
| hsa-miR-299-5p | UGGUUUACCGUCCCACAUACAU (SEQ ID NO: 15) |
| hsa-miR-3136-5p | CUGACUGAAUAGGUAGGGUCAUU (SEQ ID NO: 16) |
| hsa-miR-3150b | GAGGGAAAGCAGGCCAACCUCGAGGAUCUCCCCAGCCUUGGC GUUCAGGUGCUGAGGAGAUCGUCGAGGUUGGCCUGCUUCCCC UC (SEQ ID NO: 17) |
| hsa-miR-3160-1 | GGACCUGCCCUGGGCUUUCUAGUCUCAGCUCUCCUCCAGCUC AGCUGGUCAGGAGAGCUGAGACUAGAAAGCCCAGGGCAGGUU C (SEQ ID NO: 18) |
| hsa-miR-3160-2 | ACCUGCCCUGGGCUUUCUAGUCUCAGCUCUCCUGACCAGCUG AGCUGGAGGAGAGCUGAGACUAGAAAGCCCAGGGCAGGU (SEQ ID NO: 19) |
| hsa-miR-3188 | GGCGCCUCCUGCUCUGCUGUGCCGCCAGGGCCUCCCCUAGCGC GCCUUCUGGAGAGGCUUUGUGCGGAUACGGGGCUGGAGGCCU (SEQ ID NO: 20) |
| hsa-miR-320b-1 | AAUUAAUCCCUCUCUUUCUAGUUCUUCCUAGAGUGAGGAAAA GCUGGGUUGAGAGGGCAAACAAAUUAACUAAUUAAUU (SEQ ID NO: 21) |
| hsa-miR-335-5p | UCAAGAGCAAUAACGAAAAAUGU (SEQ ID NO: 22) |
| hsa-miR-345 | ACCCAAACCCUAGGUCUGCUGACUCCUAGUCCAGGGCUCGUG AUGGCUGGUGGGCCCUGAACGAGGGGUCUGGAGGCCUGGGUU UGAAUAUCGACAGC (SEQ ID NO: 23) |
| hsa-miR-34b-5p | UAGGCAGUGUCAUUAGCUGAUUG (SEQ ID NO: 24) |
| hsa-miR-3613-3p | ACAAAAAAAAAAGCCCAACCCUUC (SEQ ID NO: 25) |
| hsa-miR-3616 | UGUCACUCCGCCAGCAUCAUGAAGUGCACUCAUGAUAUGUUU GCCCCAUCAGCGUGUCACGAGGGCAUUUCAUGAUGCAGGCGG GGUUGGCA (SEQ ID NO: 26) |
| hsa-miR-3689a-3p | CUGGGAGGUGUGAUAUCGUGGU (SEQ ID NO: 27) |
| hsa-miR-378b | ACUGGACUUGGAGGCAGAA (SEQ ID NO: 28) |
| hsa-miR-3910-1 | CUUUUGCUGUCAGUUUUUCUGUUGCUUGUCUUGGUUUUAUGC CUUUUAUAUCAAGGCACAUAAAAGGCAUAAAACCAAGACAAG CAACAAAAAAAGGAUUGAUCACAGAAG (SEQ ID NO: 29) |
| hsa-miR-3934-5p | UCAGGUGUGGAAACUGAGGCAG (SEQ ID NO: 30) |
| hsa-miR-4306 | UGGAGAGAAAGGCAGUA (SEQ ID NO: 31) |
| hsa-miR-4313 | AGCCCCCUGGCCCCAAACCC (SEQ ID NO: 32) |
| hsa-miR-4325 | UUGCACUUGUCUCAGUGA (SEQ ID NO: 33) |
| hsa-miR-4431 | UGGUUUGCGACUCUGAAAACUAGAAGGUUUAUGACUGGGCA UUUCUCACCCAAUGCCCAAUAUUGAACUUUCUAGUUGUCAGA GUCAUUAACCC (SEQ ID NO: 34) |
| hsa-miR-4445 | UUCCUGCAGAUUGUUUCUUUUGCCGUGCAAGUUUAAGUUUUU GCACGGCAAAAGAAACAAUCCAGAGGGU (SEQ ID NO: 35) |
| hsa-miR-4487 | ACUGUCCUUCAGCCAGAGCUGGCUGAAGGGCAGAAGGGAACU GUCCUUCAGCCAGAGCUGGCUGAAGGGCAGA (SEQ ID NO: 36) |
| hsa-miR-450b-5p | UUUUGCAAUAUGUUCCUGAAUA (SEQ ID NO: 37) |
| hsa-miR-455-3p | GCAGUCCAUGGGCAUAUACAC (SEQ ID NO: 38) |

TABLE 1-continued

| microRNA/small RNA name | microRNA Sequence |
|---|---|
| hsa-miR-4672 | GGCUGCUUCUCGCCUCUGUCCAGCUGUGUGGCCUUGGACAAG CCUCUUGGUUACACAGCUGGACAGAGGCACGAAACAGCC (SEQ ID NO: 39) |
| hsa-miR-4685-5p | CCCAGGGCUUGGAGUGGGGCAAGGUU (SEQ ID NO: 40) |
| hsa-miR-4708-3p | AGCAAGGCGGCAUCUCUCUGAU (SEQ ID NO: 41) |
| hsa-miR-4749-5p | UGCGGGGACAGGCCAGGGCAUC (SEQ ID NO: 42) |
| hsa-miR-4769-3p | UCUGCCAUCCUCCCUCCCCUAC (SEQ ID NO: 43) |
| hsa-miR-4771 | AGCAGACUUGACCUACAAUUA (SEQ ID NO: 44) |
| hsa-miR-4788 | AAUGAAGGAUUACGGACCAGCUAAGGGAGGCAUUAGGAUCCU UAUUCUUGCCUCCCUUAGUUGGUCCCUAAUCCUUCGUU (SEQ ID NO: 45) |
| hsa-miR-4791 | UGGAUAUGAUGACUGAAA (SEQ ID NO: 46) |
| hsa-miR-4797-5p | GACAGAGUGCCACUUACUGAA (SEQ ID NO: 47) |
| hsa-miR-500a-3p | AUGCACCUGGGCAAGGAUUCUG (SEQ ID NO: 48) |
| hsa-miR-509-3p | UGAUUGGUACGUCUGUGGGUAG (SEQ ID NO: 49) |
| hsa-miR-510-5p | UACUCAGGAGAGUGGCAAUCAC (SEQ ID NO: 50) |
| hsa-miR-520a-5p | CUCCAGAGGGAAGUACUUUCU (SEQ ID NO: 51) |
| hsa-miR-520g | UCCCAUGCUGUGACCCUCUAGAGGAAGCACUUUCUGUUUGUU GUCUGAGAAAAAACAAAGUGCUUCCCUUUAGAGUGUUACCGU UUGGGA (SEQ ID NO: 52) |
| hsa-miR-520h | UCCCAUGCUGUGACCCUCUAGAGGAAGCACUUUCUGUUUGUU GUCUGAGAAAAAACAAAGUGCUUCCCUUUAGAGUUACUGUUU GGGA (SEQ ID NO: 53) |
| hsa-miR-532 | CGACUUGCUUUCUCUCCUCCAUGCCUUGAGUGUAGGACCGUU GGCAUCUUAAUUACCUCCCACACCCAAGGCUUGCAGAAGAG CGAGCCU (SEQ ID NO: 54) |
| hsa-miR-548aa | AAAAACCACAAUUACUUUUGCACCA (SEQ ID NO: 55) |
| hsa-miR-548ac | CAAAACCGGCAAUUACUUUUG (SEQ ID NO: 56) |
| hsa-miR-548ae | CAAAAACUGCAAUUACUUUCA (SEQ ID NO: 57) |
| hsa-miR-548ag | AAAGGUAAUUGUGGUUUCUGC (SEQ ID NO: 58) |
| hsa-miR-548aj-3p | UAAAAACUGCAAUUACUUUUA (SEQ ID NO: 59) |
| hsa-miR-548ap-3p | AAAAACCACAAUUACUUUU (SEQ ID NO: 60) |
| hsa-miR-548au | AAAAGUAAUUGCGGUUUUUGCUAUUGGUUUUAAUGGCAGUU ACUUUUGCACCAG (SEQ ID NO: 61) |
| hsa-miR-548k | AAAAGUACUUGCGGAUUUUGCU (SEQ ID NO: 62) |
| hsa-miR-548t-3p | AAAAACCACAAUUACUUUUGCACCA (SEQ ID NO: 63) |
| hsa-miR-548x-3p | UAAAAACUGCAAUUACUUUC (SEQ ID NO: 64) |
| hsa-miR-548y | GCCUAAACUAUUAGGUUGGUGCAAAAGUAAUCACUGUUUUU GCCAUUACUCUCAGUGGCAAAAACCGUGAUUACUUUUGCACC AACCUAGUAACACCUUCACUGUGGGGG (SEQ ID NO: 65) |
| hsa-miR-561 | CUUCAUCCACCAGUCCUCCAGGAACAUCAAGGAUCUUAAACU UUGCCAGAGCUACAAAGGCAAAGUUUAAGAUCCUUGAAGUUC CUGGGGGAACCAU (SEQ ID NO: 66) |
| hsa-miR-603 | CACACACUGCAAUUACUUUUGC (SEQ ID NO: 67) |
| hsa-miR-606 | AAACUACUGAAAAUCAAAGAU (SEQ ID NO: 68) |
| hsa-miR-6075 | GACACCACAUGCUCCUCCAGGCCUGCCUGCCCUCCAGGUCAU GUUCCAGUGUCCCACAGAUGCAGCACCACGGCCCAGGCGGCA UUGGUGUCACC (SEQ ID NO: 69) |

TABLE 1-continued

| microRNA/small RNA name | microRNA Sequence |
|---|---|
| hsa-miR-6081 | CCACCACGGUGCUGGCACCAGGGCCUCUGCCCCGUAGGACAC CGAGGCUUAUGAAUAGGAGCAGUGCCGGCCAAGGCGCCGGCA CCAUCUUGGUGAU (SEQ ID NO: 70) |
| hsa-miR-6739-5p | UGGGAAAGAGAAAGAACAAGUA (SEQ ID NO: 71) |
| hsa-miR-6749-5p | UCGGGCCUGGGGUUGGGGGAGC (SEQ ID NO: 72) |
| hsa-miR-6776 | CGGGCUCUGGGUGCAGUGGGGGUUCCCACGCCGCGGCAACCA CCACUGUCUCUCCCCAG (SEQ ID NO: 73) |
| hsa-miR-6782-5p | UAGGGGUGGGGGAAUUCAGGGGUGU (SEQ ID NO: 74) |
| hsa-miR-6793-5p | UCCCCAACCCCUGCCCGCAG (SEQ ID NO: 75) |
| hsa-miR-6850 | GUGCGGAACGCUGGCCGGGGCGGGAGGGGAAGGGACGCCCGG CCGGAACGCCGCACUCACG (SEQ ID NO: 76) |
| hsa-miR-6865-3p | ACACCCUCUUUCCCUACCGCC (SEQ ID NO: 77) |
| hsa-miR-6873-5p | CAGAGGGAAUACAGAGGGCAAU (SEQ ID NO: 78) |
| hsa-miR-7706 | UGGAGCUGUGUGCAGGGCCAGCGCGGAGCCCGAGCAGCCGCG GUGAAGCGCCUGUGCUCUGCCGAGA (SEQ ID NO: 79) |
| hsa-miR-7973 | UGUGACCCUAGAAUAAUUAC (SEQ ID NO: 80) |
| hsa-miR-8052 | CGGGACUGUAGAGGGCAUGAGC (SEQ ID NO: 81) |
| hsa-miR-8075 | CCUUGCUGAUGGCAGAUGUCGGAUCUGCCUCGCUUAUACGUG CCCUUGCUGAUGGCAGAUGUCGGGUCUGCCUCGCUUAU (SEQ ID NO: 82) |
| hsa-miR-8089 | AAGGAGCACUCACUCCAAUUUCCCUGGACUGGGGGCAGGCUG CCACCUCCUGGGGACAGGGGAUUGGGGCAGGAUGUUCCAG (SEQ ID NO: 83) |
| hsa-miR-892b | UGCAAUGCCCUACUCAGAAAGGUGCCAUUUAUGUAGAUUUUA UGUCACUGGCUCCUUUCUGGGUAGAGCAAGGCUCA (SEQ ID NO: 84) |
| hsa-miR-936 | ACAGUAGAGGGAGGAAUCGCAG (SEQ ID NO: 85) |
| hsa-miR-937-5p | GUGAGUCAGGGUGGGGCUGG (SEQ ID NO: 86) |
| scaRNA17 | AGAGGCUUGGGCCGCCGAGCUGGACCCGGACCGGUUUUGGGU ACUGUACUGGGGGCAGGGCAGAGAGGG (SEQ ID NO: 87) |
| U6 | GUGCUCGCUUCGGCAGCACAUAUACUAAAAUUGGAACGAUAC AGAGAAGAUUAGCAUGGCCCCUGCGCAAGGAUGACACGCAAA UUCGUGAAGCGUUCCAUAUUUU (SEQ ID NO: 88) |

Example 1

Expression of Human Mature miRNAs by qPCR in Sample Cohort of 45 AD Patients and 182 Controls The mean log fold change for hsa-miR-335-5p, hsa-miR-3613-3p and hsa-miR-6865-3p PARKmiRs between AD patients and healthy controls are illustrated in FIG. 1.

Example 2

Analyses of PARKmiR Combinations, hsa-miR-335-5p/hsa-miR-3613-3p, hsa-miR-3613-3p/hsa-miR-6865-3p and hsa-miR-335-5p/hsa-miR-6865-3p in Sample Cohort of 45 AD Patients and 182 Controls The qPCR technique of Example 1 was used to identify potential diagnostic biomarkers. It was determined that combinations of PARKmiRs show high predictability for AD diagnosis. The results of the model with hsa-miR-335-5p/hsa-miR-6865-3p, hsa-miR-335-5p/hsa-miR-3613-3p and hsa-miR-6865-3p/hsa-miR-3613-3p between AD patients and healthy controls are illustrated in FIG. 2.

Example 3

It is evidenced that any combination of three or more microRNAs from the list of 85 identified miRNAs can be used to diagnose the occurrence of AD in patients.

Example 4

Measurement of levels of a combination of two or more miRNAs in serum from patients can assist in distinctly differentiating between a potential AD patient and a healthy individual. A serum sample is obtained from blood withdrawn from patients suspected of AD. The serum is used for total microRNA isolation and enrichment. This RNA would then be tested using qPCR to measure the levels of any two or more of the 85 miRNAs mentioned in Example 1, or any one of three miRNAs mentioned in Examples 5-7. Detectable levels of any two or more of the 85 miRNAs or any one of the three miRNAs confirms the patient has AD. If desired, other sample fluids may be utilized, including plasma, venous or arterial blood, or CSF samples withdrawn by lumbar puncture. Such plasma, blood or CSF samples are processed as discussed above regarding serum, e.g., so as to provide a sample for processing and evaluation outside the human or animal body. It will be understood that measurement of more than two miRNAs in combination or a set of combinations used in a test matrix may desirably increase the accuracy of AD diagnosis. Following diagnosis, the result is then communicated to the patient.

Example 5

Since a combination of miRNA can be used for diagnosis it may be advisable to test all the candidates to eliminate any cohort-based variation. It is understood that any detectable amounts of relevant miRNA will indicate AD pathology. However, those of ordinary skill in the art recognize it may be clinically helpful to use values of 45 v 182 samples to set an artificial threshold for diagnosis. Differential miRNA levels can be used to develop diagnostic biomarker kits that can be used by clinicians in diagnosis as well as in clinical trials. In this study the presence and quantification of miRNA from serum was determined by qRT-PCR which amplifies and quantifies the RNA is question. Other suitable techniques known to those of ordinary skill herein may be alternatively utilized, including use of labeled antisense sequences and labeled antibodies. Suitable antibodies are preferentially selective, referring to a binding reaction between two molecules that is typically more than 10 to 100 times background molecular associations under measurement conditions. Thus, under designated immunoassay conditions, the specified antibodies bind to a particular miRNA sequence, thereby identifying its presence. Specific binding to an antibody under such conditions requires an antibody that is selected for its specificity for a particular miRNA. For example, antibodies raised against a particular miRNA can be selected by subtracting out antibodies that cross-react with other molecules. A variety of immunoassay formats may be used to select antibodies specifically immunoreactive with a particular miRNA including solid-phase ELISA immunoassays (see, e.g., Harlow & Lane, Antibodies, A Laboratory Manual (1988) for a description of immunoassay formats and conditions that can be used to determine specific immunoreactivity). Methods for determining whether two molecules specifically interact are disclosed therein, and methods of determining binding affinity and specificity are well known in the art (see, for example, Harlow and Lane, Antibodies: A laboratory manual (Cold Spring Harbor Laboratory Press, 1988); Friefelder, "Physical Biochemistry: Applications to biochemistry and molecular biology" (W.H. Freeman and Co. 1976)). The term "antibody" as used herein encompasses naturally occurring antibodies as well as non-naturally occurring antibodies, including, for example, single chain antibodies, chimeric, bifunctional and humanized antibodies, as well as antigen-binding fragments thereof, (e.g., Fab', F(ab')2, Fab, Fv and rIgG). See also, Pierce Catalog and Handbook, 1994-1995 (Pierce Chemical Co., Rockford, Ill.). See also, e.g., Kuby, J., Immunology, 3rd Ed., W.H. Freeman & Co., New York (1998). Such non-naturally occurring antibodies can be constructed using solid phase peptide synthesis, can be produced recombinantly or can be obtained, for example, by screening combinatorial libraries consisting of variable heavy chains and variable light chains as described by Huse et al., Science, Vol. 246 (1989) 1275-81. These and other methods of making, for example, chimeric, humanized, CDR-grafted, single chain, and bifunctional antibodies are well known to those skilled in the art (Winter and Harris, Immunol. Today, Vol. 14 (1993) 243-46; Ward et al., Nature, Vol. 341 (1989) 544-46; Harlow and Lane, supra, 1988; Hilyard et al., Protein Engineering: A practical approach (IRL Press 1992); Borrabeck, Antibody Engineering, 2d ed. (Oxford University Press 1995). Methods for producing both monoclonal and polyclonal antibodies from identified RNA sequences are well known in the art.

Example 6

Many neurodegenerative diseases are closely related to each other when it comes to symptoms as well as pathological markers. The circulating diagnostic markers for one neurodegenerative disease can be useful for diagnosis of other disease. A method to diagnose other neurodegenerative diseases like Parkinson's Disease, Dementia with Lewy body (DLB), Amyotrophic lateral sclerosis (ALS), Multiple system atrophy (MSA), CorticoBasal Degeneration (CBD), Progressive Supranuclear Palsy (PSP) can also be developed using similar miRNA measurements of candidates mentioned above. Disease specific kits can be developed similar to that mentioned above with various combinations of miRNAs listed in [0019].

Example 7

The miRNAs detected in one or more combinations can regulate several proteins in the cells. Novel protein targets for AD can be discovered using these microRNAs and their combinations. The involvement of these proteins in AD etiology can be further established to target them for therapy.

Example 8

We have experimentally confirmed the predicted regulation of LRRK2 by hsa-miR-335-5p and SNCA by hsa-miR-3613-3p in dopaminergic neuronal cell lines. Therapeutic intervention to regulate the novel targets mentioned can be achieved by RNA interference technologies.

Example 9

Small nucleic acid molecules derived from miRNAs mentioned above will be designed to therapeutically intervene by specifically targeting genes in AD brains to achieve complete or partial remedy. The effects discussed above will be achieved for precise targeting in brain cells.

What is claimed is:

1. A method, comprising the steps of:
   (a) providing a serum sample from a human patient;
   (b) detecting the level of SEQ ID NOs: 22, 25, and 27 in the serum sample;
   (c) diagnosing the human patient with Alzheimer's disease when the level of SEQ ID NOs: 22, 25 and 77 in the serum sample are decreased in comparison to the level of SEQ ID NOs: 22, 25, and 77 in control serum samples obtained from healthy patients; and
   (e) administering a cholinesterase inhibitor or a N-methyl-D-aspartate receptor antagonist to said human patient diagnosed with Alzheimer's disease.

2. The method of claim 1, further comprising detecting the level of one or more miRNA selected from the group consisting of SEQ ID NOs: 2-21, 23, 24, 26-76 and 78-86 within said serum sample.

3. The method according to claim 2, wherein said one or more miRNA comprises SEQ ID NO: 15.

4. The method according to claim 2, wherein said one or more miRNA comprises SEQ ID NO: 21.

5. The method according to claim 2, wherein said one or more miRNA comprises SEQ ID NO: 24.

6. The method according to claim 2, wherein said one or more miRNA comprises SEQ ID NO: 52.

7. The method according to claim 2, wherein said one or more miRNA comprises SEQ ID NO: 54.

8. The method according to claim 2, wherein said at least one further miRNA comprises SEQ ID NO: 55.

9. The method of claim 1, further comprising detecting the level of one or more miRNA selected from the group consisting of SEQ ID NOs: 2, 3, 5, 6, 7, 8, 9, 10, 11, 12, 13, 14, 15, 16, 24, 27, 28, 31, 30, 32, 33, 37, 38, 40, 42, 43, 44, 46, 47, 48, 49, 50, 51, 55, 56, 57, 58, 59, 60, 62, 63, 64, 67, 68, 71, 72, 74, 75, 78, 80, 81, 85 and 86 within said serum sample.

10. The method of claim 1, further comprising detecting the level of one or more miRNA selected from the group consisting of SEQ ID NOs: 4, 17, 18, 19, 20, 21, 23, 26, 29, 34, 35, 36, 39, 45, 52, 53, 54, 61, 65, 66, 69, 70, 73, 76, 79, 82, 83 and 84 within said serum sample.

11. The method of claim 1, further comprising detecting the level of one or more miRNA selected from the group consisting of SEQ ID NOs: 15, 21, 24, 52, 54 and 55 within said serum sample.

12. The method of claim 1, further comprising detecting the level of two or more miRNA selected from the group consisting of SEQ ID NOs: 2-21, 23, 24, 26-76 and 78-86 within said serum sample.

13. The method of claim 1, further comprising detecting the level of two or more miRNA selected from the group consisting of SEQ ID NOs: 2, 3, 5, 6, 7, 8, 9, 10, 11, 12, 13, 14, 15, 16, 24, 27, 28, 31, 30, 32, 33, 37, 38, 40, 42, 43, 44, 46, 47, 48, 49, 50, 51, 55, 56, 57, 58, 59, 60, 62, 63, 64, 67, 68, 71, 72, 74, 75, 78, 80, 81, 85 and 86 within said serum sample.

14. The method of claim 1, further comprising detecting the level of two or more miRNA selected from the group consisting of SEQ ID NOs: 4, 17, 18, 19, 20, 21, 23, 26, 29, 34, 35, 36, 39, 45, 52, 53, 54, 61, 65, 66, 69, 70, 73, 76, 79, 82, 83 and 84 within said serum sample.

15. The method of claim 1, further comprising detecting the level of two or more miRNA selected from the group consisting of SEQ ID NOs: 15, 21, 24, 52, 54 and 55 within said serum sample.

16. The method according to claim 1, wherein said cholinesterase inhibitor is donepezil, galantamine or rivastigmine.

17. The method according to claim 1, wherein said N-methyl-D-aspartate receptor antagonist is memantine.

* * * * *

UNITED STATES PATENT AND TRADEMARK OFFICE
CERTIFICATE OF CORRECTION

PATENT NO. : 11,634,775 B2
APPLICATION NO. : 16/623937
DATED : April 25, 2023
INVENTOR(S) : Simon Geir Moller et al.

It is certified that error appears in the above-identified patent and that said Letters Patent is hereby corrected as shown below:

On the Title Page

Item (56) OTHER PUBLICATIONS

"Liang (BMC Genomics 2007 8:166 pp.1-20)" should read --Liang, Y. et al., Characterization of micro RNA expression profiles in normal human tissues. BMC Genomics, Vol. 8, No. 166 (June 2007), 1-20.--

"Lugli (PLOS ONE 10(10) e0139233 pp. 1-18 Oct. 2015).*" should read --Lugli, G. et al. Plasma Exosomal miRNAs in Persons with and without Alzheimer Disease: Altered Expression and Prospects for Biomarkers. PloS One, Vol. 10, No. 10 (Oct. 2015), 1-18. e0139233.--

"Wang (PloS ONE Jul. 2012 7(7);e41561).*" should read --Wang, E. et al., Comparing the microRNA spectrum between serum and plasma, PloS One, Vol. 7, No. 7 (2012) e41561. *--

"Wolenski (Journal of Applied Toxicology 2017; 37:278-286).*" should read --Wolenski, F. et al., Identification of microRNA biomarker candidates in urine and plasma from rats with kidney or liver damage, Journal of Applied Toxicology, Vol. 37 (2017), 278-86. *--

"Geekiyanage et al., "Blood serum miRNA: Non-invasive biomarkers for Alzheimer's disease", Experimental Neurology, vol. 235, No. 2 (2012) 491-6." should read --Geekiyanage, H. et al., Blood serum miRNA: Non-invasive biomarkers for Alzheimer's disease. Experimental Neurology, Vol. 235, No. 2 (June 2012), 491-96.--

"Li, Fei et al., MicroRNA-574 is involved in cognitive impairment in 5-month-old APP/PS1 mice through regulation of neuritin, Brain Research 2015, vol. 1627, pp. 177-188" should read --Li, F. et al., MicroRNA is involved in cognitive impairment in 5-month-old APP/PSI mice through regulation of neuritin. Brain Research, Vol. 1627 (2015), 177-88.--

Signed and Sealed this
Twelfth Day of September, 2023

Katherine Kelly Vidal
*Director of the United States Patent and Trademark Office*

CERTIFICATE OF CORRECTION (continued)
U.S. Pat. No. 11,634,775 B2

In the Specification

Column 1
Line 34, "makes it even complex to" should read --make it complex even to--
Line 37, "and AD related dementia currently affects" should read --and AD-related dementia currently affect--
Lines 41-42, "multi-drug regiment" should read --multi-drug regimens--
Lines 42-43, "Antidepressants, Anxiolytics, Antipsychotic" should read --antidepressants, anxiolytics, antipsychotic--
Line 46, "and processes including" should read --and processes, including--
Line 48, "receptor amongst others" should read --receptor, among others--

Column 2
Line 17, "MicroRNAs ("miRNAs) are" should read --MicroRNAs (miRNAs) are--
Lines 28-29, "approximately 70 nucleotide precursor" should read --approximately 70- nucleotide precursor--
Line 33, "Exportin-5 where it is" should read --Exportin-5, where it is--
Line 35, "in the RNA Induced Silencing Complex resulting" should read --in the RNA-induced silencing complex, resulting--
Line 37, "Nature 2004; MAcRae" should read --Nature 2004; MacRae--
Line 40, "silencing complex RISC" should read --silencing complex (RISC)--
Line 59, "Koval et al," should read --Koval et al.,--
Line 60, "miRNA has been" should read --miRNAs have been--
Line 61, "and thus presents" should read --and thus to present--
Line 62, "Chen et al," should read --Chen et al.,--

Column 3
Lines 11-12, "PARKmiR-NAs" should read --PARK-miRNAs--
Lines 14-15, "healthy con-trols" should read --healthy con-trols.--
Line 25, "control and PD" should read --control and Parkinson's disease (PD)--
Line 32, "project we also tested" should read --project, we also tested--
Line 39, "Unexpectedly the" should read --Unexpectedly, the--
Line 42, "used were valid we tested" should read --used were valid, we tested--
Line 44, "and AD serum both" should read --and AD serum, both--
Line 45, "in abundance validating" should read --in abundance, validating--
Line 53, "(DemVest study) which" should read --(DemVest study), which--
Line 59, "Nov. 1, 2004 and 31 Aug. 2006 it" should read --Nov. 1, 2004 and Aug. 31, 2006, it--
Line 60, "Parkinson Disease" should read --Parkinson's disease--
Line 61, "of the study 212" should read --of the study, 212--

Column 4
Line 1, "score>15))." should read --score > 15).--
Line 13, "ARDRA" should be --ADRDA--
Line 16, "for elderly and were" should read --for the elderly, and were--
Line 19, "phase serum" should read --phase, serum--
Line 19, "controls were selected" should read --controls was selected--

CERTIFICATE OF CORRECTION (continued)
U.S. Pat. No. 11,634,775 B2

Line 22, "collected at the same" should read --collected on the same--
Line 35, "3000 · g to remove" should read --3000 x g to remove--
Line 37, "RNA Isolation," should read --RNA isolation,--
Line 46, "from ParkWest project 45 AD from" should read --from the ParkWest project and 45 AD from--
Line 47, "as described above, they were" should read --as described above. The RNA was--
Line 53, "samples were quantified" should read --samples was quantified--
Line 62, "(p<0.05)" should read --(p < 0.05)--
Line 66, "for miRNA specific qPCR" should read --for miRNA-specific qPCR--

Column 5
Line 1, "following manufacturer's protocol and" should read --following the manufacturer's protocol, and--
Line 2, using miRNA specific" should read --using miRNA-specific--
Lines 4-5, "were used reference" should read --were used as reference--
Line 9, "color Real-Time" should read --Color Real-Time--
Line 11, "$R^2$=0.97882" should read --$R^2$ = 0.97882--
Line 20, "with log transformed" should read --with log-transformed--
Line 22, "from The Norwegian" should read --from the Norwegian--

Column 6
Line 5, "hsa-miR-93'7-5p" should read --hsa-miR-937-5p--
Line 11, "hsa-miR-4'708-3p" should read --hsa-miR-4708-3p--
Line 25, "hsa-miR-93'7-5p" should read --hsa-miR-937-5p--

Column 11
Line 56, "controls are illustrated" should read --controls is illustrated--

Column 13
Line 6, "miRNAs confirms the" should read --miRNAs confirm the--
Lines 21-22, "used for diagnosis it may" should read --used for diagnosis, it may--
Line 26, "values of 45 v 182" should read --values of 45 versus 182--
Line 32, "serum was determined" should read --serum were determined--
Line 33, "the RNA is question." should read --the RNA in question.--
Line 51, "particular RNA including" should read --particular RNA, including--
Line 62, "and Co. 1976))." should read --and Co. (1976)).--
Line 65, "single chain antibodies" should read --single-chain antibodies--

Column 14
Line 1, "thereof, (e.g.," should read --thereof (e.g.,--
Lines 1-2, "See also, Pierce" should read --See also Pierce--
Line 4, "3$^{rd}$ Ed.," should read --3$^{rd}$ ed.,--
Line 14, "single chain, and" should read --single-chain, and--
Line 21, "Press 1995)." should read --Press 1995)).--
Lines 28-29, "closely related to each other when it" should read --closely related when it--
Line 32, "other disease." should read --another disease.--

Line 33, "Parkinson's Disease" should read --Parkinson's disease--
Lines 34-36, "Amyotropic lateral sclerosis (ALS), Multiple system atrophy (MSA), CorticoBasal Degeneration (CBD), Progressive Supranuclear Palsy" should read --amyotropic lateral sclerosis (ALS), multiple system atrophy (MSA), corticobasal degeneration (CBD), and progressive supranuclear palsy--
Line 38, "Disease specific kits" should read --Disease-specific kits--

In the Claims

Column 39
Line 20, "(c) administering" should read --(d) administering--
Line 42, "24, 27, 28, 31, 30, 32" should read --24, 27, 28, 30, 31, 32--

Column 40
Line 27, "24, 27, 28, 31, 30, 32" should read --24, 27, 28, 30, 31, 32--

SEQUENCE LISTING

<160> NUMBER OF SEQ ID NOS: 88

<210> SEQ ID NO 1
<211> LENGTH: 22
<212> TYPE: RNA
<213> ORGANISM: Homo sapien

<400> SEQUENCE: 1
ucaccgggug uaaaucagcu ug                                          22

<210> SEQ ID NO 2
<211> LENGTH: 79
<212> TYPE: RNA
<213> ORGANISM: Homo sapien

<400> SEQUENCE: 2
cccgggcuga gguaggaggu uguauaguug aggaggacac ccaaggagau cacuauacgg  60
ccuccuagcu uuccccagg                                               79

<210> SEQ ID NO 3
<211> LENGTH: 23
<212> TYPE: RNA
<213> ORGANISM: Homo sapien

<400> SEQUENCE: 3
ccugcagcga cuugauggcu ucc                                         23

<210> SEQ ID NO 4
<211> LENGTH: 111
<212> TYPE: RNA
<213> ORGANISM: Homo sapien

<400> SEQUENCE: 4
ccacgguccu aguuaaaaag gcacauuccu agacccugcc ucagaacuac ugaacagagu  60
cacugggugu ggaguccagg aaucugcauu uuuaccccua ucgccccgc c           111

<210> SEQ ID NO 5
<211> LENGTH: 22
<212> TYPE: RNA
<213> ORGANISM: Homo sapien

<400> SEQUENCE: 5
ucaaaacuga ggggcauuuu cu                                          22

<210> SEQ ID NO 6
<211> LENGTH: 22
<212> TYPE: RNA
<213> ORGANISM: Homo sapien

<400> SEQUENCE: 6
gcuauuucac gacaccaggg uu                                          22

<210> SEQ ID NO 7
<211> LENGTH: 22
<212> TYPE: RNA
<213> ORGANISM: Homo sapien

<400> SEQUENCE: 7
cuccuacaua uuagcauuaa ca                                          22

<210> SEQ ID NO 8
<211> LENGTH: 22

```
<212> TYPE: RNA
<213> ORGANISM: Homo sapien

<400> SEQUENCE: 8
ccaauauuac ugugcugcuu ua                                            22

<210> SEQ ID NO 9
<211> LENGTH: 23
<212> TYPE: RNA
<213> ORGANISM: Homo sapien

<400> SEQUENCE: 9
aacauucauu gcugucggug ggu                                           23

<210> SEQ ID NO 10
<211> LENGTH: 21
<212> TYPE: RNA
<213> ORGANISM: Homo sapien

<400> SEQUENCE: 10
cuauauauca aacauauucc u                                             21

<210> SEQ ID NO 11
<211> LENGTH: 21
<212> TYPE: RNA
<213> ORGANISM: Homo sapien

<400> SEQUENCE: 11
augaccuaug aauugacaga c                                             21

<210> SEQ ID NO 12
<211> LENGTH: 22
<212> TYPE: RNA
<213> ORGANISM: Homo sapien

<400> SEQUENCE: 12
accuggcaua caauguagau uu                                            22

<210> SEQ ID NO 13
<211> LENGTH: 24
<212> TYPE: RNA
<213> ORGANISM: Homo sapien

<400> SEQUENCE: 13
agcgcgggcu gagcgcugcc aguc                                          24

<210> SEQ ID NO 14
<211> LENGTH: 21
<212> TYPE: RNA
<213> ORGANISM: Homo sapien

<400> SEQUENCE: 14
auccccagau acaaggaca a                                              21

<210> SEQ ID NO 15
<211> LENGTH: 22
<212> TYPE: RNA
<213> ORGANISM: Homo sapien

<400> SEQUENCE: 15
ugguuuaccg ucccacauac au                                            22

<210> SEQ ID NO 16
```

```
<211> LENGTH: 23
<212> TYPE: RNA
<213> ORGANISM: Homo sapien

<400> SEQUENCE: 16
cugacugaau agguagggguc auu                                          23

<210> SEQ ID NO 17
<211> LENGTH: 86
<212> TYPE: RNA
<213> ORGANISM: Homo sapien

<400> SEQUENCE: 17
gagggaaagc aggccaaccu cgaggaucuc cccagccuug gcguucaggu gcugaggaga   60
ucgucgaggu uggccugcuu ccccuc                                       86

<210> SEQ ID NO 18
<211> LENGTH: 85
<212> TYPE: RNA
<213> ORGANISM: Homo sapien

<400> SEQUENCE: 18
ggaccugccc ugggcuuucu agucucagcu cuccuccagc ucagcugguc aggagagcug   60
agacuagaaa gcccagggca gguuc                                        85

<210> SEQ ID NO 19
<211> LENGTH: 81
<212> TYPE: RNA
<213> ORGANISM: Homo sapien

<400> SEQUENCE: 19
accugcccug ggcuuucuag ucucagcucu ccugaccagc ugagcuggag gagagcugag   60
acuagaaagc ccagggcagg u                                            81

<210> SEQ ID NO 20
<211> LENGTH: 85
<212> TYPE: RNA
<213> ORGANISM: Homo sapien

<400> SEQUENCE: 20
ggcgccuccu gcucugcugu gccgccaggg ccuccccuag cgcgccuucu ggagaggcuu   60
ugugcggaua cggggcugga ggccu                                        85

<210> SEQ ID NO 21
<211> LENGTH: 79
<212> TYPE: RNA
<213> ORGANISM: Homo sapien

<400> SEQUENCE: 21
aauuaauccc ucucuuucua guucuuccua gagugaggaa aagcugggu gagagggcaa    60 acaaauuaac uaauuaauu                                               79

<210> SEQ ID NO 22
<211> LENGTH: 23
<212> TYPE: RNA
<213> ORGANISM: Homo sapien

<400> SEQUENCE: 22
ucaagagcaa uaacgaaaaa ugu                                          23
```

```
<210> SEQ ID NO 23
<211> LENGTH: 98
<212> TYPE: RNA
<213> ORGANISM: Homo sapien

<400> SEQUENCE: 23
acccaaaccc uaggucugcu gacuccuagu ccagggcucg ugauggcugg ugggcccuga      60 acgaggggguc uggaggccug gguuugaaua ucgacagc                             98

<210> SEQ ID NO 24
<211> LENGTH: 23
<212> TYPE: RNA
<213> ORGANISM: Homo sapien

<400> SEQUENCE: 24
uaggcagugu cauuagcuga uug                                              23

<210> SEQ ID NO 25
<211> LENGTH: 24
<212> TYPE: RNA
<213> ORGANISM: Homo sapien

<400> SEQUENCE: 25
acaaaaaaaa aagcccaacc cuuc                                             24

<210> SEQ ID NO 26
<211> LENGTH: 92
<212> TYPE: RNA
<213> ORGANISM: Homo sapien

<400> SEQUENCE: 26
ugucacuccg ccagcaucau gaagugcacu caugauaugu uugccccauc agcgugucac      60
gagggcauuu caugaugcag gcggggguugg ca                                   92

<210> SEQ ID NO 27
<211> LENGTH: 22
<212> TYPE: RNA
<213> ORGANISM: Homo sapien

<400> SEQUENCE: 27
cugggaggug ugauaucgug gu                                               22

<210> SEQ ID NO 28
<211> LENGTH: 19
<212> TYPE: RNA
<213> ORGANISM: Homo sapien

<400> SEQUENCE: 28
acuggacuug gaggcagaa                                                   19

<210> SEQ ID NO 29
<211> LENGTH: 111
<212> TYPE: RNA
<213> ORGANISM: Homo sapien

<400> SEQUENCE: 29
cuuuugcugu caguuuuucu guugcuuguc uugguuuuau gccuuuuaua ucaaggcaca      60
uaaaaggcau aaaaccaaga caagcaacaa aaaaaggauu gaucacagaa g              111

<210> SEQ ID NO 30
<211> LENGTH: 22
<212> TYPE: RNA
```

```
<213> ORGANISM: Homo sapien

<400> SEQUENCE: 30
ucaggugugg aaacugaggc ag                                         22

<210> SEQ ID NO 31
<211> LENGTH: 17
<212> TYPE: RNA
<213> ORGANISM: Homo sapien

<400> SEQUENCE: 31
uggagagaaa ggcagua                                               17

<210> SEQ ID NO 32
<211> LENGTH: 20
<212> TYPE: RNA
<213> ORGANISM: Homo sapien

<400> SEQUENCE: 32
agcccccugg ccccaaaccc                                            20

<210> SEQ ID NO 33
<211> LENGTH: 18
<212> TYPE: RNA
<213> ORGANISM: Homo sapien

<400> SEQUENCE: 33
uugcacuugu cucaguga                                              18

<210> SEQ ID NO 34
<211> LENGTH: 94
<212> TYPE: RNA
<213> ORGANISM: Homo sapien

<400> SEQUENCE: 34
ugguuugcga cucugaaaac uagaagguuu augacugggc auuucucacc caaugcccaa    60
uauugaacuu ucuaguuguc agagucauua accc                               94

<210> SEQ ID NO 35
<211> LENGTH: 70
<212> TYPE: RNA
<213> ORGANISM: Homo sapien

<400> SEQUENCE: 35
uuccugcaga auguuucuuu ugccgugcaa guuuaaguuu uugcacggca aaagaaacaa    60
uccagagggu                                                          70

<210> SEQ ID NO 36
<211> LENGTH: 73
<212> TYPE: RNA
<213> ORGANISM: Homo sapien

<400> SEQUENCE: 36 acugccuuc agccagagcu ggcugaaggg cagaagggaa cuguccuuca gccagagcug     60
gcugaagggc aga                                                      73

<210> SEQ ID NO 37
<211> LENGTH: 22
<212> TYPE: RNA
<213> ORGANISM: Homo sapien
```

```
<400> SEQUENCE: 37
uuuugcaaua uguuccugaa ua                                              22

<210> SEQ ID NO 38
<211> LENGTH: 21
<212> TYPE: RNA
<213> ORGANISM: Homo sapien

<400> SEQUENCE: 38
gcaguccaug ggcauauaca c                                               21

<210> SEQ ID NO 39
<211> LENGTH: 81
<212> TYPE: RNA
<213> ORGANISM: Homo sapien

<400> SEQUENCE: 39
ggcugcuucu cgccucuguc cagcugugug gccuuggaca agccucuugg uuacacagcu     60
ggacagaggc acgaaacagc c                                               81

<210> SEQ ID NO 40
<211> LENGTH: 26
<212> TYPE: RNA
<213> ORGANISM: Homo sapien

<400> SEQUENCE: 40
cccagggcuu ggagugggc aagguu                                          26

<210> SEQ ID NO 41
<211> LENGTH: 22
<212> TYPE: RNA
<213> ORGANISM: Homo sapien

<400> SEQUENCE: 41
agcaaggcgg caucucucug au                                              22

<210> SEQ ID NO 42
<211> LENGTH: 22
<212> TYPE: RNA
<213> ORGANISM: Homo sapien

<400> SEQUENCE: 42
ugcggggaca ggccagggca uc                                              22

<210> SEQ ID NO 43
<211> LENGTH: 22
<212> TYPE: RNA
<213> ORGANISM: Homo sapien

<400> SEQUENCE: 43
ucugccaucc ucccucccu ac                                               22

<210> SEQ ID NO 44
<211> LENGTH: 21
<212> TYPE: RNA
<213> ORGANISM: Homo sapien

<400> SEQUENCE: 44
agcagacuug accuacaauu a                                               21

<210> SEQ ID NO 45
```

```
<211> LENGTH: 80
<212> TYPE: RNA
<213> ORGANISM: Homo sapien

<400> SEQUENCE: 45
aaugaaggau uacggaccag cuaagggagg cauuaggauc cuuauucuug ccucccuuag    60
uuggucccua auccuucguu                                               80

<210> SEQ ID NO 46
<211> LENGTH: 18
<212> TYPE: RNA
<213> ORGANISM: Homo sapien

<400> SEQUENCE: 46
uggauaugau gacugaaa                                                 18

<210> SEQ ID NO 47
<211> LENGTH: 21
<212> TYPE: RNA
<213> ORGANISM: Homo sapien

<400> SEQUENCE: 47
gacagagugc cacuuacuga a                                             21

<210> SEQ ID NO 48
<211> LENGTH: 22
<212> TYPE: RNA
<213> ORGANISM: Homo sapien

<400> SEQUENCE: 48
augcaccugg gcaaggauuc ug                                            22

<210> SEQ ID NO 49
<211> LENGTH: 22
<212> TYPE: RNA
<213> ORGANISM: Homo sapien

<400> SEQUENCE: 49
ugauugguac gucuguggu ag                                             22

<210> SEQ ID NO 50
<211> LENGTH: 22
<212> TYPE: RNA
<213> ORGANISM: Homo sapien

<400> SEQUENCE: 50
uacucaggag aguggcaauc ac                                            22

<210> SEQ ID NO 51
<211> LENGTH: 21
<212> TYPE: RNA
<213> ORGANISM: Homo sapien

<400> SEQUENCE: 51
cuccagaggg aaguacuuuc u                                             21

<210> SEQ ID NO 52
<211> LENGTH: 90
<212> TYPE: RNA
<213> ORGANISM: Homo sapien
```

```
<400> SEQUENCE: 52
ucccaugcug ugacccucua gaggaagcac uuucuguuug uugucugaga aaaaacaaag    60
ugcuucccuu uagaguguua ccguuuggga                                    90

<210> SEQ ID NO 53
<211> LENGTH: 88
<212> TYPE: RNA
<213> ORGANISM: Homo sapien

<400> SEQUENCE: 53
ucccaugcug ugacccucua gaggaagcac uuucuguuug uugucugaga aaaaacaaag    60
ugcuucccuu uagaguuacu guuuggga                                      88

<210> SEQ ID NO 54
<211> LENGTH: 91
<212> TYPE: RNA
<213> ORGANISM: Homo sapien

<400> SEQUENCE: 54
cgacuugcuu ucucuccucc augccuugag uguaggaccg uuggcaucuu aauuacccuc    60
ccacacccaa ggcuugcaga agagcgagcc u                                  91

<210> SEQ ID NO 55
<211> LENGTH: 25
<212> TYPE: RNA
<213> ORGANISM: Homo sapien

<400> SEQUENCE: 55
aaaaaccaca auuacuuuug cacca                                         25

<210> SEQ ID NO 56
<211> LENGTH: 22
<212> TYPE: RNA
<213> ORGANISM: Homo sapien

<400> SEQUENCE: 56
caaaaaccgg caauuacuuu ug                                            22

<210> SEQ ID NO 57
<211> LENGTH: 21
<212> TYPE: RNA
<213> ORGANISM: Homo sapien

<400> SEQUENCE: 57
caaaaacugc aauuacuuuc a                                             21

<210> SEQ ID NO 58
<211> LENGTH: 21
<212> TYPE: RNA
<213> ORGANISM: Homo sapien

<400> SEQUENCE: 58
aaagguaauu gugguuucug c                                             21

<210> SEQ ID NO 59
<211> LENGTH: 21
<212> TYPE: RNA
<213> ORGANISM: Homo sapien
```

```
<400> SEQUENCE: 59
uaaaaacugc aauuacuuuu a                                              21

<210> SEQ ID NO 60
<211> LENGTH: 19
<212> TYPE: RNA
<213> ORGANISM: Homo sapien

<400> SEQUENCE: 60
aaaaaccaca auuacuuuu                                                 19

<210> SEQ ID NO 61
<211> LENGTH: 54
<212> TYPE: RNA
<213> ORGANISM: Homo sapien

<400> SEQUENCE: 61
aaaaguaauu gcgguuuuug cuauugguuu uaauggcagu uacuuuugca ccag           54

<210> SEQ ID NO 62
<211> LENGTH: 22
<212> TYPE: RNA
<213> ORGANISM: Homo sapien

<400> SEQUENCE: 62
aaaaguacuu gcggauuuug cu                                             22

<210> SEQ ID NO 63
<211> LENGTH: 25
<212> TYPE: RNA
<213> ORGANISM: Homo sapien

<400> SEQUENCE: 63
aaaaaccaca auuacuuuug cacca                                          25

<210> SEQ ID NO 64
<211> LENGTH: 20
<212> TYPE: RNA
<213> ORGANISM: Homo sapien

<400> SEQUENCE: 64
uaaaaacugc aauuacuuuc                                                20

<210> SEQ ID NO 65
<211> LENGTH: 110
<212> TYPE: RNA
<213> ORGANISM: Homo sapien

<400> SEQUENCE: 65
gccuaaacua uuagguuggu gcaaaaguaa ucacuguuuu ugccauuacu cucaguggca     60
aaaaccguga uuacuuuugc accaaccuag uaacaccuuc acugugggg               110

<210> SEQ ID NO 66
<211> LENGTH: 97
<212> TYPE: RNA
<213> ORGANISM: Homo sapien

<400> SEQUENCE: 66
cuucauccac caguccucca ggaacaucaa ggaucuuaaa cuuugccaga gcuacaaagg     60
caaaguuuaa gauccuugaa guuccugggg gaaccau                             97
```

```
<210> SEQ ID NO 67
<211> LENGTH: 22
<212> TYPE: RNA
<213> ORGANISM: Homo sapien

<400> SEQUENCE: 67
cacacacugc aauuacuuuu gc                                              22

<210> SEQ ID NO 68
<211> LENGTH: 21
<212> TYPE: RNA
<213> ORGANISM: Homo sapien

<400> SEQUENCE: 68
aaacuacuga aaaucaaaga u                                               21

<210> SEQ ID NO 69
<211> LENGTH: 95
<212> TYPE: RNA
<213> ORGANISM: Homo sapien

<400> SEQUENCE: 69
gacaccacau gcuccuccag gccugccugc ccuccagguc auguuccagu gucccacaga     60
ugcagcacca cggcccaggc ggcauuggug ucacc                                95

<210> SEQ ID NO 70
<211> LENGTH: 97
<212> TYPE: RNA
<213> ORGANISM: Homo sapien

<400> SEQUENCE: 70
ccaccacggu gcuggcacca gggccucugc cccguaggac accgaggcuu augaauagga     60
gcagugccgg ccaaggcgcc ggcaccaucu uggugau                              97

<210> SEQ ID NO 71
<211> LENGTH: 22
<212> TYPE: RNA
<213> ORGANISM: Homo sapien

<400> SEQUENCE: 71
ugggaaagag aaagaacaag ua                                              22

<210> SEQ ID NO 72
<211> LENGTH: 22
<212> TYPE: RNA
<213> ORGANISM: Homo sapien

<400> SEQUENCE: 72
ucgggccugg gguuggggga gc                                              22

<210> SEQ ID NO 73
<211> LENGTH: 59
<212> TYPE: RNA
<213> ORGANISM: Homo sapien

<400> SEQUENCE: 73
cgggcucugg gugcaguggg gguucccacg ccgcggcaac caccacuguc ucucccag       59

<210> SEQ ID NO 74
<211> LENGTH: 25
<212> TYPE: RNA
<213> ORGANISM: Homo sapien
```

<400> SEQUENCE: 74 uaggggugggg ggaauucagg ggugu                                    25

<210> SEQ ID NO 75
<211> LENGTH: 20
<212> TYPE: RNA
<213> ORGANISM: Homo sapien

<400> SEQUENCE: 75 uccccaacccc cugcccgcag                                          20

<210> SEQ ID NO 76
<211> LENGTH: 61
<212> TYPE: RNA
<213> ORGANISM: Homo sapien

<400> SEQUENCE: 76
gugcggaacg cuggccgggg cgggaggga agggacgccc ggccggaacg ccgcacucac   60
g                                                                 61

<210> SEQ ID NO 77
<211> LENGTH: 21
<212> TYPE: RNA
<213> ORGANISM: Homo sapien

<400> SEQUENCE: 77
acacccucuu ucccuaccgc c                                          21

<210> SEQ ID NO 78
<211> LENGTH: 22
<212> TYPE: RNA
<213> ORGANISM: Homo sapien

<400> SEQUENCE: 78
cagagggaau acagagggca au                                         22

<210> SEQ ID NO 79
<211> LENGTH: 67
<212> TYPE: RNA
<213> ORGANISM: Homo sapien

<400> SEQUENCE: 79
uggagcugug ugcagggcca gcgcggagcc cgagcagccg cggugaagcg ccugugcucu   60
gccgaga                                                           67

<210> SEQ ID NO 80
<211> LENGTH: 20
<212> TYPE: RNA
<213> ORGANISM: Homo sapien

<400> SEQUENCE: 80
ugugacccua gaauaauuac                                            20

<210> SEQ ID NO 81
<211> LENGTH: 22
<212> TYPE: RNA
<213> ORGANISM: Homo sapien

<400> SEQUENCE: 81
cgggacugua gagggcauga gc                                         22

```
<210> SEQ ID NO 82
<211> LENGTH: 80
<212> TYPE: RNA
<213> ORGANISM: Homo sapien

<400> SEQUENCE: 82
ccuugcugau ggcagauguc ggaucugccu cgcuuauacg ugcccuugcu gauggcagau    60
gucgggucug ccucgcuuau                                                80

<210> SEQ ID NO 83
<211> LENGTH: 82
<212> TYPE: RNA
<213> ORGANISM: Homo sapien

<400> SEQUENCE: 83
aaggagcacu cacuccaauu ucccuggacu gggggcaggc ugccaccucc ugggacagg     60 ggauuggggc aggauguucc ag                                             82

<210> SEQ ID NO 84
<211> LENGTH: 77
<212> TYPE: RNA
<213> ORGANISM: Homo sapien

<400> SEQUENCE: 84
ugcaaugccc uacucagaaa ggugccauuu auguagauuu uaugucacug gcuccuuucu    60
ggguagagca aggcuca                                                   77

<210> SEQ ID NO 85
<211> LENGTH: 22
<212> TYPE: RNA
<213> ORGANISM: Homo sapien

<400> SEQUENCE: 85
acaguagagg gaggaaucgc ag                                             22

<210> SEQ ID NO 86
<211> LENGTH: 20
<212> TYPE: RNA
<213> ORGANISM: Homo sapien

<400> SEQUENCE: 86
gugagucagg gugggggcugg                                               20

<210> SEQ ID NO 87
<211> LENGTH: 69
<212> TYPE: RNA
<213> ORGANISM: Homo sapien

<400> SEQUENCE: 87
agaggcuugg gccgccgagc uggacccgga ccgguuuugg guacuguacu ggggcaggg     60 cagagaggg                                                            69

<210> SEQ ID NO 88
<211> LENGTH: 106
<212> TYPE: RNA
<213> ORGANISM: Homo sapien
```

```
<400> SEQUENCE: 88
gugcucgcuu cggcagcaca uauacuaaaa uuggaacgau acagagaaga uuagcauggc        60
cccugcgcaa ggaugacacg caaauucgug aagcguucca uauuuu                     106
```